(12) United States Patent
Kamiyama et al.

(10) Patent No.: US 7,580,553 B2
(45) Date of Patent: Aug. 25, 2009

(54) MEDICAL IMAGING APPARATUS

(75) Inventors: Naohisa Kamiyama, Tochigi-ken (JP); Tetsuya Higashi, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 506 days.

(21) Appl. No.: 11/109,813

(22) Filed: Apr. 20, 2005

(65) Prior Publication Data

US 2005/0248587 A1 Nov. 10, 2005

(30) Foreign Application Priority Data

Apr. 21, 2004 (JP) ............... 2004-124984

(51) Int. Cl.
G06K 9/00 (2006.01)
G06K 9/36 (2006.01)
(52) U.S. Cl. ..................... 382/128; 382/284
(58) Field of Classification Search ................ 382/128, 382/284; 345/632
See application file for complete search history.

(56) References Cited

U.S. PATENT DOCUMENTS

| | | | | |
|---|---|---|---|---|
| 4,885,634 | A * | 12/1989 | Yabe ............ | 348/71 |
| 6,328,693 | B1 * | 12/2001 | Miyatake et al. ....... | 600/437 |
| 6,544,179 | B1 * | 4/2003 | Schmiesing et al. ..... | 600/447 |
| 2001/0031102 | A1 * | 10/2001 | Lunetta et al. ........ | 382/284 |
| 2002/0102031 | A1 * | 8/2002 | Lafage et al. ......... | 382/284 |
| 2002/0115941 | A1 * | 8/2002 | Whayne et al. ........ | 600/523 |
| 2002/0126890 | A1 * | 9/2002 | Katayama et al. ...... | 382/154 |
| 2003/0097065 | A1 * | 5/2003 | Lee et al. ........... | 600/437 |
| 2004/0130645 | A1 * | 7/2004 | Ohmura et al. ..... | 348/333.08 |
| 2007/0004980 | A1 * | 1/2007 | Warner et al. ......... | 600/411 |

FOREIGN PATENT DOCUMENTS

| | | |
|---|---|---|
| JP | 3014733 | 6/1995 |
| JP | 2000-22928 | 1/2000 |
| JP | 2000-022928 * | 1/2000 |
| JP | 3079708 | 6/2001 |

* cited by examiner

*Primary Examiner*—Bhavesh M Mehta
*Assistant Examiner*—John B Strege
(74) *Attorney, Agent, or Firm*—Oblon, Spivak, McClelland, Maier & Neustadt, P.C.

(57) ABSTRACT

A medical imaging apparatus includes an imaging unit, a first processor, a second processor, a display unit, and an output unit. The imaging unit is configured to image a subject. The first processor is configured to prepare an image data based on the imaging unit. The second processor is configured to combine the image data and a decorative data. The display unit is configured to display the combined image data. The output unit is configured to output the combined image data as a decorated image data.

25 Claims, 11 Drawing Sheets

MEDICAL IMAGING APPARATUS

CROSS-REFERENCE TO RELATED APPLICATION

This application is based upon and claims the benefit of priority from prior Japanese Patent Application No. P2004-124984, filed on Apr. 21, 2004, the entire contents of which are incorporated herein by reference.

BACKGROUND OF THE INVENTION

1. Field of the Invention

The present invention relates to a medical imaging apparatus for, a medical image display apparatus for, and a method of providing an image data. The present invention also relates to a computer readable medium on which is stored a program module for providing an image data.

2. Discussion of the Background

Medical diagnosis images are usually presented to a patient so that a doctor and the patient can share information of the images. This is important in terms of an informed consent. In some cases, the patient may be given a copy of the images, particularly when the patient was imaged by an ultrasound diagnosis apparatus. Some reasons of giving the patient ultrasound diagnosis images occasionally but more often compared to other medical images may be as follows:

(a) The images may be given as a record of fetus (and embryo) growth when an ultrasound diagnosis apparatus is used for an obstetrical service;

(b) It is easy to treat and provide the images to the patient since the image size is similar to that of a general-purpose photograph; and (c) The images are easily printed out and given to the patient since the images can be printed out from an accompanying printer right on the spot and even during an examination with the ultrasound diagnosis apparatus.

Meanwhile, an instant photo machine to make tiny stickers called 'print club' (trademark) stickers is known and described, for example, in Japanese Utility Model Registration No. U3014733. In this machine, a camera shoots a subject (usually a person) and a resulting image is synthesized with a predetermined decorative image which has been stored in the machine. The synthesized image sticker is printed out on the spot right away. The decorative image is an image to become a subject for the synthesis with the shot image. The decorative image may usually feature popular characters of cartoon or the like. The decorative image may also have a shape of a frame. When a plurality of decorative images have been prepared in advance, the person as a user of the machine may be allowed to select one of the decorative images according to his or her preference. The decorative image may alternatively feature a specific local area such as, for example, a tourist spot so that a synthesized image sticker can be commemorative of the tourist spot.

The ultrasound diagnosis image is occasionally given to the patient. However, such ultrasound diagnosis image is neither decorated nor interesting to see compared to the 'print club' (trademark) sticker. This is because the ultrasound diagnosis image is originally and basically prepared for the diagnostic purpose.

Medical images which are imaged by a medical imaging apparatus such as, for example, an X-ray diagnosis apparatus, an X-rat computed tomography apparatus, a magnetic resonance imaging apparatus, a nuclear medicine diagnosis apparatus, an ultrasound diagnosis apparatus, an endoscope, or the like provides an internal condition of the patient. Therefore, it is not possible to apply the instant photo machine described above to the medical images.

Nowadays, personal computers have been major instruments in the office and even privately. If one uses an image scanning device coupled to a personal computer and scans the printed out medical image, it may not be difficult to take in the medical image into the personal computer as digital data. Since there is quite a number of software for the personal computer for image synthesis, it may be possible to decorate the medical image with other image in the personal computer.

However, it is cumbersome for the patient to take in the medical image given by the doctor into the personal computer. In terms of this problem, the synthesizing operation is provided in business as a commercial service. Whether privately or in business, the medical image taken-in by the scanning device is likely to deteriorate its image quality. The image quality is quite important since the medical image usually shows details of the internal condition of the patient as long as the medical image is desired to be kept as something to show the internal condition even if it is just for the commemorative purpose. In addition, the medical image typically includes and shows imaging condition information and patient information. Therefore, if the patient brings the medical image to the commercial service shop for the image decoration synthesis, his or her personal information turns out to be known to assistants in the service shop.

The medical image(s) given to the patient by the doctor may not be the patient's desired image(s). For example, when the given medical image shows a fetus in an expecting mother as the patient, she would like to have an image showing her fetus well from her point of view but may not have a chance to choose one she likes.

Interpretation of the medical image usually requires highly skill and expert knowledge, addis almost impossible for an ordinary person including the patient and the assistants in the service shop. For example, when the medical image shows an organ including a tumor, neither of the patient or the assistants knows where the tumor is in the medical image. Also for example, when the medical image shows a fetus, neither of the patient or the assistants knows where a heart of the fetus is in the medical image. Although the doctor may explain to the patient where the tumor or the heart is, the patient may forget it later or it may be difficult for the patient to remember it.

SUMMARY OF THE INVENTION

According to the first aspect of the present invention, there is provided a medical imaging apparatus. The apparatus includes an imaging unit, a first processor, a second processor, a display unit, and an output unit. The imaging unit is configured to image a subject. The first processor is configured to prepare an image data based on the imaging unit. The second processor is configured to combine the image data and a decorative data. The display unit is configured to display the combined image data. The output unit is configured to output the combined image data as a decorated image data.

According to the second aspect of the present invention, there is provided a medical image display apparatus for use in a medical facility. The apparatus includes a receiving unit, a memory unit, a processor, a display unit, and an output unit. The receiving unit is configured to receive a medical image data. The memory unit is configured to store a decorative data. The processor is configured to combine the medical image data and the decorative data. The display unit is configured to display the combined image data. The output unit is configured to output the combined image data as a decorated image data.

According to the third aspect of the present invention, there is provided a method of providing an image data. The method begins by imaging a subject in a medical imaging apparatus and preparing the image data based on the imaging. The method continues by combining the image data and a decorative data. The method still continues by displaying the combined image data and outputting the combined image data as a decorated image data.

According to the fourth aspect of the present invention, there is provided a computer readable medium on which is stored a program module for providing an image data obtained by a medical imaging apparatus. The program module has instructions, which when executed perform steps including retrieving a decorative data, combining the image data and the decorative data, displaying the combined image data, and outputting the combined image data as a decorated image data.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings.

Although an ultrasound diagnosis apparatus will be described as an example of a medical imaging apparatus, one or more of the embodiment or its modifications below may also be applied to other medical imaging apparatus such as, for example, an X-ray diagnosis apparatus, an X-ray computed tomography apparatus, a magnetic resonance imaging apparatus, a nuclear medicine diagnosis apparatus, an endoscope, or the like.

The medical imaging apparatus may be fixed on the floor of an examination room in a medical facility such as a hospital, a clinic, a medical practitioner's office, or the like. The medical imaging apparatus may alternatively be movable to a patient's bed or any other possible or necessary place inside the medical facility. Further, the medical imaging apparatus may also be portable to a patient's home or any other possible or necessary place outside the medical facility as well as the above places inside the medical facility.

First Embodiment

Figure 1:
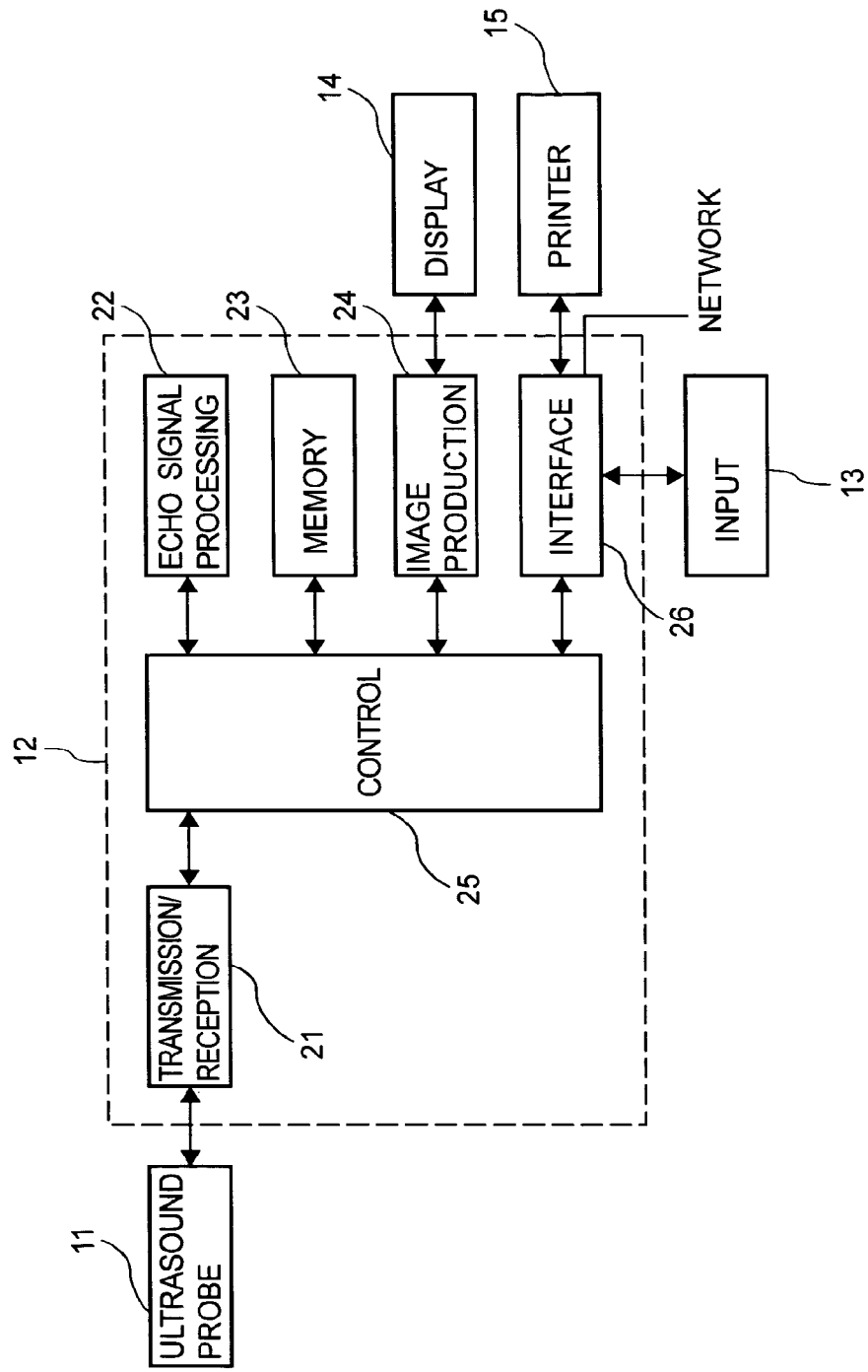
FIG. 1 is a block diagram showing an exemplary configuration of an ultrasound diagnosis apparatus according to the first embodiment.

FIG. 1 is a block diagram showing an exemplary configuration of the ultrasound diagnosis apparatus according to the first embodiment. The ultrasound diagnosis apparatus includes an ultrasound probe 11, a main unit 12, an input unit 13, a display unit 14, and a printer 15.

The ultrasound probe 11 includes a plurality of ultrasound transducers which transmits ultrasound signals to the inside of the patient and receives returning signals resulting from the ultrasound signals as echo signals.

The main unit 12 includes a transmission/reception unit 21, an echo signal processing unit 22, a memory unit 23, an image production processing unit 24, a control unit 25, and an interface 26.

The transmission/reception unit 21 and the ultrasound probe 12 may correspond to 'an imaging unit'. The transmission/reception unit 21 has transmission circuitry including a delay circuit and a pulse circuit and reception circuitry including an analog-to-digital converter and an adder. The transmission/reception unit 21 produces pulsed ultrasound signals and provides the signals to the ultrasound probe 11. The transmission/reception unit 21 receives echo signals received by the ultrasound probe 11 as a result of an ultrasound examination.

The echo signal processing unit 22 may correspond to 'a first processor'. The echo signal processing unit 22 is coupled to the transmission/reception unit 21, and conducts logarithmic amplification, envelope detection, and the like on the echo signals received by the transmission/reception unit 21 so as to convert the echo signals into data indicating signal strength of the echo signals in brightness. The echo signal processing unit 22 prepares image data so that a diagnosis image originated from the echo signals is usually placed in the center of an ultrasound image to be displayed in the display unit 14. The center of the ultrasound image may correspond to a subject image part of the image data. A peripheral area of the center of the ultrasound image may correspond to 'a peripheral part' of the image data. Since the ultrasound probe 11 is typically made contact with a body surface of the patient for a certain period, the resulting image data usually represents a motion picture or the like which includes a plurality of image frames.

The memory unit 23 stores the image data and also decorative data which will be combined to the image data. The memory unit 23 may also store controlling programs of the ultrasound diagnosis apparatus to be executed by the control unit 25 and image processing programs for, for example, combining the image data and the decorative data to be executed by the image production processing unit 24

Figure 2:
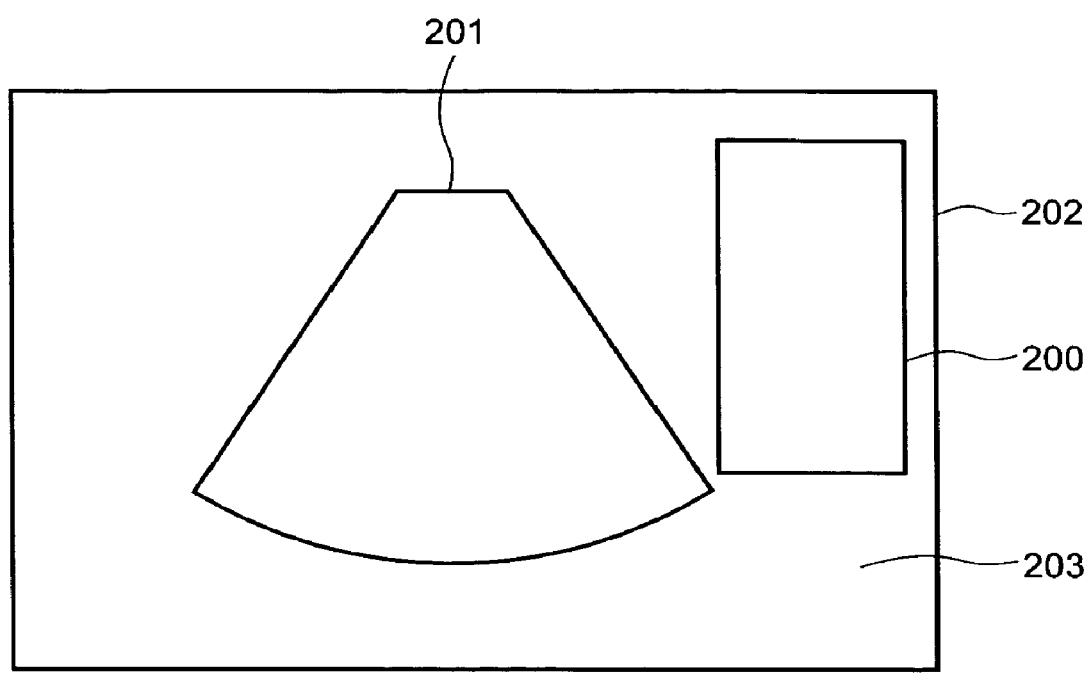
FIG. 2 is an illustration for explaining an exemplary relationship among an ultrasound image, a diagnosis image, and a decorative image based on a decorative data.

FIG. 2 is an illustration for explaining an exemplary relationship among the ultrasound image, the diagnosis image, and a decorative image based on the decorative data. As shown in FIG. 2, a decorative image 200 may be something to decorate a diagnosis image 201 in an ultrasound image 202 and be placed in a peripheral area 203 of the ultrasound image 202. The ultrasound image 202 may also be called a decorated image after decorated with the decorative image as shown in FIG. 2.

The decorative image based on the decorative data may be placed in a part of the peripheral area of the ultrasound image or be formed of a frame surrounding the diagnosis image. The decorative image may alternatively be placed with the diagnosis image side by side in the ultrasound image. The decorative image may include, for example, a character of cartoon or the like, or a picture for a baby if the diagnosis image shows a fetus in an expecting mother. Any decoration may be made by the decorative image.

Figure 3A:
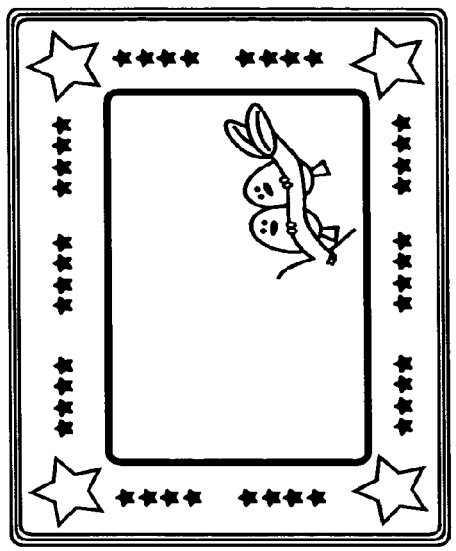
FIGS. 3A to 3D are illustrations showing examples of the decorative image.
Figure 3B:
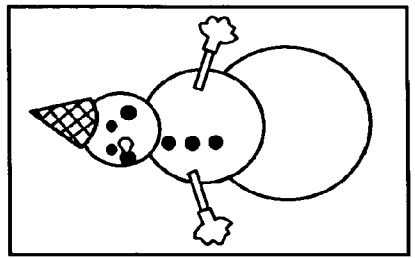

FIGS. 3A to 3D are illustrations showing examples of the decorative image. The decorative images shown in FIGS. 3A to 3D maybe be suitable for diagnosis images showing a fetus. FIGS. 3A and 3B show frame-formed decorative images, respectively. Generally, ultrasound image data includes variety of information (hereinafter referred to as accompanying information) including, for example, imaging condition information such as, for example, imaging parameters and patient information such as, for example, patient identification information and a patient name. Such accompanying information is usually displayed as a part of the ultrasound image because it is necessary for the doctor to distinguish the ultrasound image from those of other patients and to consider imaging conditions for interpreting the diagnosis image. The accompanying information, however, is usually neither necessary nor so important for the patient. Using the decorative image shown in FIG. 3A or 3B, it may be possible to cover and hide the accompanying information in the ultrasound image. This may also be advantageous for preventing other people from looking at and obtaining the accompanying information so as to protect personal information of the patient.

Figure 3C:
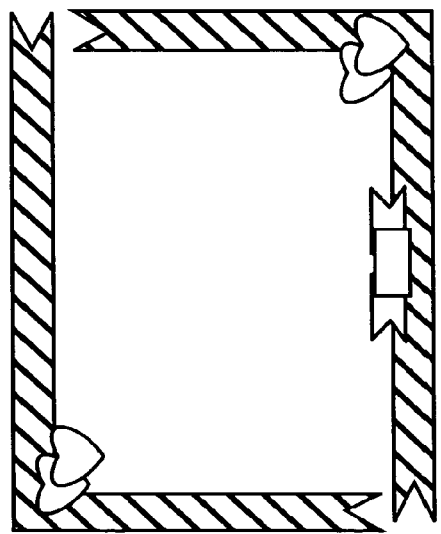
Figure 3D:
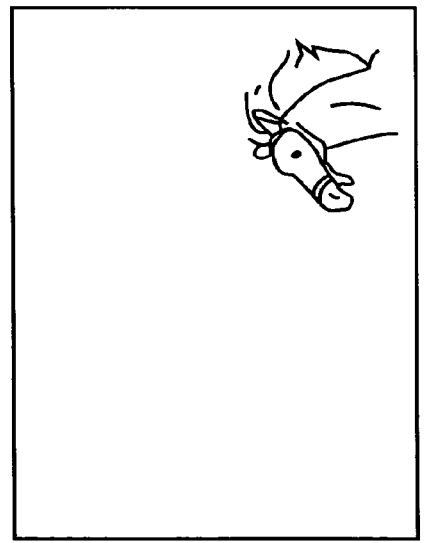

FIG. 3C is also applicable since a character placed in apart avoiding the center may not disturb the diagnosis image. FIG. 3D is also applicable when the diagnosis image and the decorative image are placed side by side or when there are two diagnosis images (e.g., a B-mode image and a Doppler-mode image) and the decorative image can be superimposed on one of the images (e.g., the Doppler-mode image).

The frame image data maybe prepared in the ultrasound diagnosis apparatus or other apparatus and taken in through the interface 26 as part of the decorative data. If a collection of images is commercially available and includes image data suitable as the decorative data, such commercially available image data may be used. The decorative data may be stored in the memory unit 23, but may be deleted from the memory unit 23 by the doctor or an operator of the ultrasound diagnosis apparatus.

The image production processing unit 24 may correspond to 'a second processor'. The image production processing unit 24 converts the image data prepared in the echo signal processing unit 22 into video signals and provides the display unit 14 with the video signals. The image production processing unit 24 also combines the image data and the decorative data so as to prepare a decorated image data. The image production processing unit 24 may synthesize the image data and the decorative data in the combination. In the combination, the image production processing unit 24 may superimpose the decorative data on the image data. When the decorative data is superimposed on the image data, the decorative data may be superimposed on the peripheral part of the image data. Alternatively, the image data may be superimposed on the decorative data. When the image data is superimposed on the decorative data, the image data may be superimposed on a superimposable part of the decorative data. The superimposable part may be, for example, a part within a frame when the decorative image based on the decorative data is formed of the frame.

The control unit 25 may correspond to 'a determination unit' with or without the image production processing unit 24. The control unit 25 may control over the ultrasound diagnosis apparatus based on the controlling programs stored in the memory unit 23. The control unit 25 may also determine a type of the ultrasound probe 11 and determine whether the decorative data is applicable to the peripheral part of the image data or not. The control unit 25 may further determine whether the image data is applicable to the superimposable part of the decorative data or not. The control unit 25 may include a CPU (central processing unit) and a system memory for storing various data needed to conduct various programs. The system memory may provide a work area needed when the programs are conducted.

The interface 26 may correspond to 'an output unit'. The interface 26 is coupled to the input unit 13 and the printer 15. The interface 26 may also be coupled to and may transmit the decorated image data to and/or receive from a personal computer, an image scanner, a digital camera, or a network. The interface 26 may write the decorated image data to and/or read from a memory medium as a memory driver. Alternatively, the interface 26 may be coupled to such a memory driver.

The input unit 13 may include one or more buttons, a keyboard, a mouse, a track ball, and/or the like so as to input information or instructions. The information or the instructions includes, for example, command information which is necessary to operate the ultrasound diagnosis apparatus and display conditions for determining a display position/size of the diagnosis image.

The display unit 14 may include a CRT (cathode ray tube) display monitor or a LCD (liquid crystal display) monitor and displays the ultrasound images and the decorated ultrasound images through the image production processing unit 24.

The printer 15 prints out the decorated image on a printing paper (or a sheet). The printer 15 may not always be necessary to be apart of the ultrasound diagnosis apparatus but may be coupled to the ultrasound diagnosis apparatus as an external device.

Figure 4:
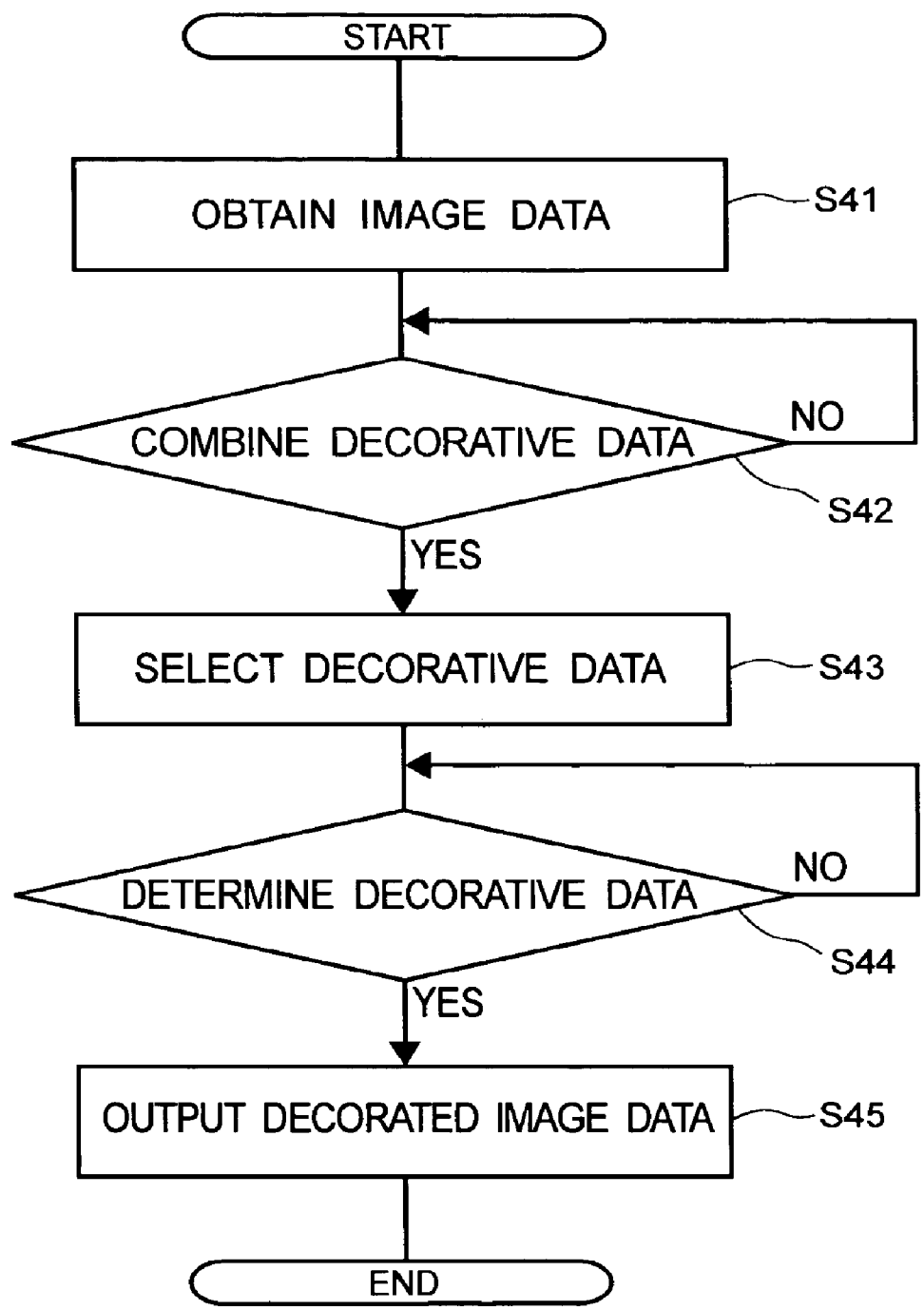
FIG. 4 is a flowchart showing an exemplary flow of a decorated image data preparation in the ultrasound diagnosis apparatus.

The ultrasound diagnosis apparatus will be operative in the following manner. FIG. 4 is a flowchart showing an exemplary flow of a decorated image data preparation in the ultrasound diagnosis apparatus.

The doctor operates the input unit 13 to input information of a diagnosis part or type (hereinafter referred to as a diagnosis type) of the patient according to a coming diagnosis type such as, for example, a fetus diagnosis or a lever diagnosis. In response to the input of the diagnosis type, an ultrasound transmission/reception condition such as, for example, an ultrasound frequency, a gain, and the like which are appropriate for the input diagnosis type is determined for the ultrasound probe 11 in the main unit 12. Since the ultrasound probe 11 is operated in the determined condition, the ultrasound signals are transmitted to the patient when the doctor contacts the ultrasound probe 11 with a body surface of the patient. The ultrasound probe 11 also receives echo signals resulting from the ultrasound transmission. The echo signals are received in the transmission/reception unit 21 and converted to image data in the echo signal processing unit 22. The image data is converted to video signals in the image production processing unit 24 and displayed as ultrasound images in the display unit 14. The ultrasound images are typically displayed as a motion picture in substantially real time.

The ultrasound images may be stored in the memory unit 23 automatically or in response to a doctor's operation of instructing to record the ultrasound images. During the real time display, the motion picture may be paused in response to a doctor's operation of instructing to pause and display one ultrasound image as a still image. The one ultrasound image may be an image frame, at a time phase corresponding to the operation, included in the ultrasound image based on the image data. It may be possible to store the image data during the display of the one ultrasound image as long as the ultrasound probe 11 is kept in contact with the body surface of the patient. The storage of the image data may be terminated in response to a doctor's operation of instructing to stop recording. The storage may alternatively be terminated automatically in response to a release of the ultrasound probe 11 from the body surface of the patient (step S41).

The doctor can diagnose the patient based on the ultrasound image displayed in the display unit 14 in real time during the ultrasound imaging. Alternatively, however, the doctor operates the input unit 13 to reproduce the stored image data for the ultrasound diagnosis. In response to the doctor's operation, the control unit 25 receives an instruction based on the doctor's operation through the interface 26 and reads the stored image data from the memory unit 23. The image data is provided to the image production processing unit 24 and displayed in the display unit 14 as the ultrasound image (or are produced ultrasound image). The doctor then conducts the ultrasound diagnosis based on the ultrasound image.

Since the ultrasound diagnosis is conducted during a display of the ultrasound images, decorated image data may be prepared (or produced) during the diagnosis. Or the decorated image data maybe prepared during explanation to the patient after the diagnosis. The doctor may select one frame image from among a number of image frames included in the image data by pausing the motion picture at one image frame. For example, if the ultrasound images show a fetus in an expecting mother, the one frame image may be selected when it shows the fetus in a preferable manner. After the pause, when the doctor inputs an instruction of combining a decorative image with the selected one frame image from the input unit 13 (step S42), the instruction is provided to the image production processing unit 24 through the interface 13 and the control unit 25. In response to the instruction, the image production processing unit 24 reads the decorative data from the memory unit 23. If there are a plurality of decorative elements as the decorative data, one of the plurality of decorative elements may be read out from the memory unit 23 and superimposed on data of the one selected frame image. The decorative-element-superimposed data is displayed as a combined image in the display unit 14. If the doctor prefers to another decorative element, the doctor may operate the input unit 13 so as to change the displayed decorative element to another one. The decorative elements may be displayed one after another in response to the doctor's operation (step S43). When one decorative element to which the doctor prefers is displayed, the doctor may operate the input unit 13 to determine the currently displayed decorative element as the decorative image (step S44). In response to the doctor's operation, the control unit 25 or the image production processing unit 24 determines decorative data corresponding to the decorative element for the selected one frame image. After the determination, the control unit 25 controls the image production processing unit 24 and the interface 26 to output the selected one frame image which is combined with the determined decorative data as the decorated image data. The decorated image data is, for example, printed out from the printer 15 so that the doctor obtains a decorated image (step S45) The output through the interface 26 is not limited to the above, but various types of outputting techniques may be applied as described in the explanation of the interface 26. In addition, the decorated image data may be stored in an IC (integrated circuit) card with a speaker. Audio information such as a message, a cardiac sound obtained during the diagnosis, and/ or the like may be stored in the IC card. The patient may be more satisfied if he/she is given such an IC card in addition to the decorated image.

Figure 5:
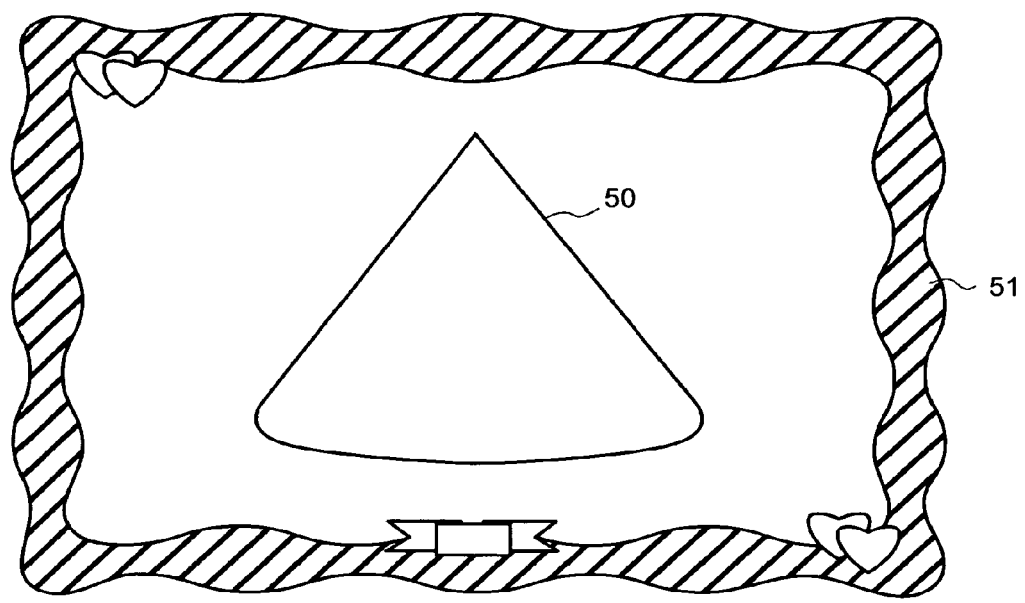
FIG. 5 is an illustration showing an example of the decorated image.

The decorated image as shown in FIG. 5 may be given to the patient from the doctor. For example, when the image shows the fetus in the expecting mother, who is the patient, the decorated image can be a commemorative of the fetus growth for the patient. In FIG. 5, a diagnosis image 50 is the selected one frame image and a decorative image 51 is the decorative image corresponding to the determined decorative element. As a whole, FIG. 5 shows the decorated image.

Compared to the conventional ultrasound image, the decorated image may become more interesting for the patient, his/her family, friends, acquaintance, and/or the like.

Although the decorative elements have been displayed one after another according to the doctor's operation, the decorative elements may alternatively be displayed in a thumbnail form. The doctor can select one decorative element by directly designating one of the decorative elements in the thumbnails. The selected decorative element maybe superimposed on the selected one frame image and a decorated image may be displayed in the display unit 13 so that the doctor can see if the selected decorative element is a preferable one.

The decorative element may be selected according to the patient's preference instead of the doctor's preference.

As described at the beginning of step S41, the information of the diagnosis type is input by the doctor. The control unit 25 may determine whether to instruct the image production processing unit 24 to prepare the decorated image data or not according to the diagnosis type. Alternatively, the control unit 25 provides the image production processing unit 24 with the information of the diagnosis type and the image production processing unit 24 may determine the same. For example, if the diagnosis type is a fetus diagnosis, the control unit 25 or the image production processing unit 24 determines that the decorated image data is prepared, but otherwise it is not prepared. Accordingly, the decorated image data is prepared for, for example, the obstetrical service in which the decorated image may be appreciated while the decorated image data is not prepared for other services in which the decorated image may not be so needed.

Although it may not be so needed to prepare the decorated image data in medical services other than the obstetrical service, the decorated image may be appreciated in such services in some cases, for example, in the case that the ultrasound image shows a healthy condition of the patient. For such services other than the obstetrical service, the memory unit 23 may store the decorative data or the decorative elements which are different from those for the obstetrical service as shown in FIGS. 6A and 6B.

Figure 6A:
FIGS. 6A and 6B are illustrations showing another example of the decorative image.
Figure 6B:
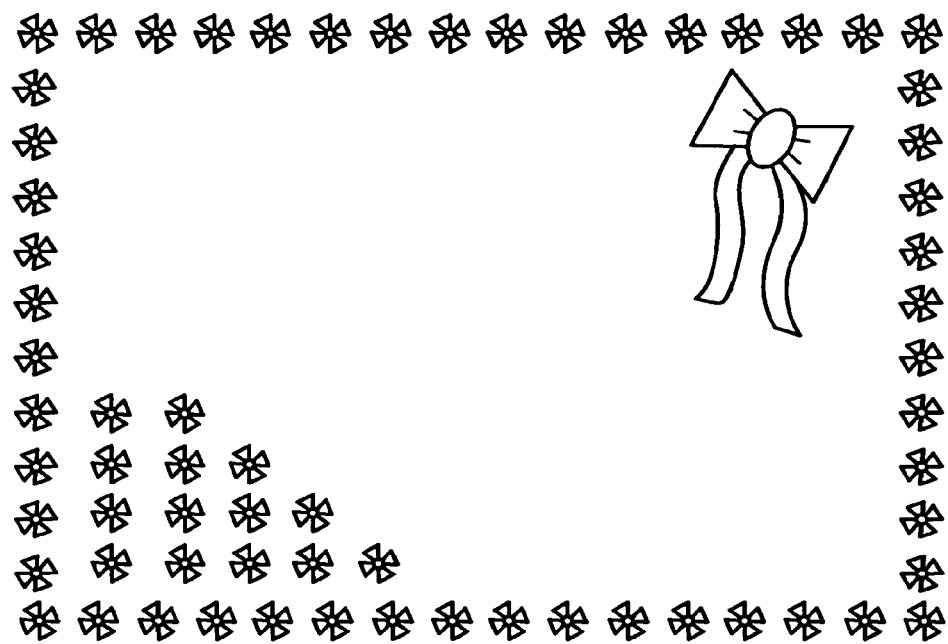

For the above control of the decorative data, the memory unit 23 stores, for example, the decorative data or the decorative elements for the fetus diagnosis as shown in FIGS. 3A to 3D in association with information of the fetus diagnosis and the decorative data or the decorative elements for the lever diagnosis as shown in FIGS. 6A and 6B in association with information of the lever diagnosis. Since the decorative data or the decorative elements which may be appropriate for each diagnosis type can be associated with the each diagnosis type, the image production processing unit 24 reads from the memory unit 23 appropriate decorative data or elements according to the input information of the diagnosis type determined by the control unit 25. Accordingly, the doctor can easily select suitable decorative data or decorative elements only by inputting the diagnosis type.

Figure 7A:
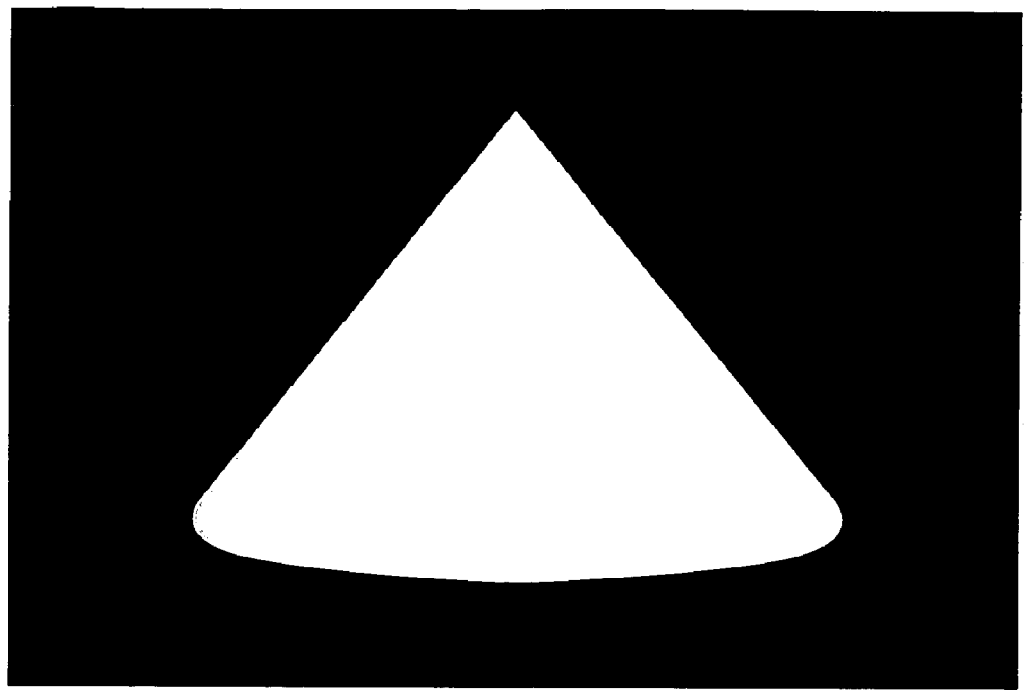
FIGS. 7A and 7B are illustrations showing exemplary diagnosis image shapes obtained by different types of an ultrasound probe.
Figure 7B:
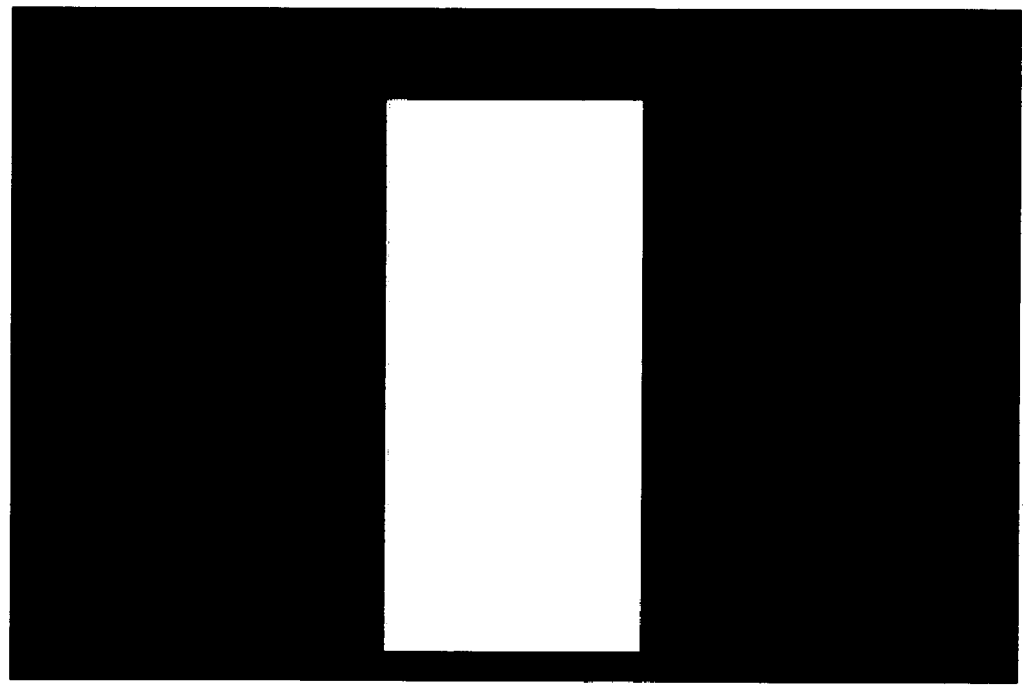

FIGS. 7A and 7B are illustrations showing exemplary diagnosis image shapes obtained by different types of the ultrasound probe 11. FIG. 7A shows a shape of a diagnosis image obtained when the ultrasound probe 11 is in a convex type which may be used to diagnose an abdominal part of the patient. FIG. 7B shows a shape of a diagnosis image obtained when the ultrasound probe 11 is in a linear type which may be used to diagnose a mammary gland part of the patient. Since the diagnosis images have different shapes according to the types of the ultrasound probe 11, the decorative data which are appropriate for the shapes may be stored for the types of the ultrasound probe 11, respectively. In the memory unit 23, information of the types of the ultrasound probe 11 may be associated with the decorative data. The control unit 25 determines the type of the ultrasound probe 11. For example, if the control unit 25 determines that it is the convex type, the control unit 25 reads the decorative data stored in association with the information of the convex type from the memory unit 23. If the control unit 25 determines that it is the linear type, the decorative data of the decorative image similar to one in FIG. 3D may be read out from the memory unit 23.

The determination of the type of the ultrasound probe 11 may be made as follows. When the ultrasound probe 11 is used, the ultrasound probe 11 is coupled to the main unit 12. Therefore, if the ultrasound probe 11 is coupled to the main unit 12 in a different condition according to the type of the ultrasound probe 11, the different condition may be recognized by the control unit 25 and the control unit 25 determines the type of the ultrasound probe 11 in accordance with the recognized condition. For example, a connecting section of the main unit 12 may have a plurality of pins. The convex type of the ultrasound probe 11 may be coupled to the main unit 12 through some of the pins. On the other hand, the linear type of the ultrasound probe 11 may be coupled to the main unit 12 through some of the pins at least one of which is different from the pins used by the convex type of the ultrasound probe 11. According to the determination of the ultrasound probe type and storage of the decorative data in association with the information of the ultrasound probe type, it may be possible to directly or easily select and combine the decorative data which is appropriate for the ultrasound probe type.

Further, the diagnosis image is displayed as a part of the ultrasound image. The shape, size, position, and the like of the diagnosis image may be determined based on the type of the ultrasound probe 11 and various imaging conditions input from the input unit 13. As described above, the decorative data can be selected in accordance with the ultrasound probe type and/or the diagnosis type. Even if so, the decorative data may not be appropriate for the diagnosis image or the ultrasound image in size. For example, when some ultrasound images have less peripheral area than others, one decorative image may cover and hide a part of a diagnosis image in such an ultrasound image and cannot be appropriate for the ultrasound image although the same decorative image may be suitable for other ultrasound images. Therefore, the control unit 25 may determine the peripheral part of the image data based on the type of the ultrasound probe 11 and the imaging conditions input from the input unit 13. The control unit 25 compares the decorative data to the peripheral part and determines whether the decorative data is applicable to the peripheral part or not. If the control unit 25 has determined that one or more decorative data are applicable to the peripheral part, the control unit 25 controls the image production processing unit 24 to prepare decorated image data with the one or more decorative data. The prepared decorated image data are displayed as the decorated image(s) in the display unit 14. If, however, the control unit 25 has determined that other decorative data are not applicable to the peripheral part, the control unit 25 does not control or allow the image production processing unit 24 to prepare decorated image data with such other decorative data. This may be helpful to avoid outputting the decorated image in which a part of the diagnosis image is covered or hidden by the decorative image. The determination in the control unit 25 may alternatively be conducted in the image production processing unit 24.

Alternatively, a size of the diagnosis image data may be reduced in order to avoid the same from happening. For example, the decorative data may include a data header which stores size information of a superimposable part where the image data of the diagnosis image can be applied in the decorative data. The size information may include a horizontal size and a vertical size. The control unit 25 compares a size of the image data of the diagnosis image to a size of the superimposable part of the decorative data and determines whether the image data is applicable to the superimposable part of the decorative data or not. If the control unit 25 has determined that the image data is not applicable to the superimposable part of the decorative data, the control unit 25 controls the image production processing unit 24 to reduce a size of the image data into an applicable size to the superimposable part. After the reduction, the image production processing unit 24 may prepare decorated image data with the decorative data. The determination in the control unit 25 may alternatively be conducted in the image production processing unit 24.

Second Embodiment

In the second embodiment, the decorated image includes more information which may be interesting to and satisfy the patient. Basic operations of preparing the decorated image data may be similar to those described in the first embodiment. Therefore, some detailed explanation which is or substantially common between the first and second embodiments will be omitted in the following description.

Photographs, comments, and/or annotations can be added to the image data as another decorative element(s) of the decorative data.

Photographs of the doctor and/or the patient may be taken, for example, by a digital camera or maybe already taken and stored in a memory card. The photographs are taken into the main unit 12 from the digital camera or the memory card through the interface 26 and stored as the decorative elements in the memory unit 23. The decorative elements of the photographs are associated with the image data of the patient since these decorative elements are used particularly for the patient.

The memory unit 23 may store arrangement information indicating where to arrange the decorative elements with respect to the image data. The arrangement information may be determined in advance or in accordance with the input from the input unit 13 by the doctor and/or the patient. A plurality of types of arrangement information may be prepared in advance or according to the input. When a plurality of types of the arrangement information are stored in the memory unit 23, the doctor (or the patient) can select one type of the arrangement information. The image production processing unit 24 arranges the decorative elements of the photographs, the comments, and the annotation based on the selected arrangement information with respect to the image data, and combines the decorative elements and the image data. Practically, the comments and/or the annotation input by the doctor and/or the patient may be inserted into the arranged positions based on the arrangement information.

The doctor and/or the patient may input comments including, but not limited to, messages, opinions, and impressions of the doctor and/or the patient from the input unit 13. The doctor may input his/her professional opinions on the image as a doctor. The doctor may explain the image in his/her opinions. The patient may input his/her impression at the time of imaging. If the image shows a fetus, the doctor and/or the patient may leave messages to the fetus at the time of the imaging. The comments input from the input unit 13 are taken into the main unit 12 through the interface 26. When the comments are stored as the decorative data in the memory unit 23, the decorative element of each comment is associated with the image data of the patient since these decorative elements are used particularly for the image.

Figure 8:
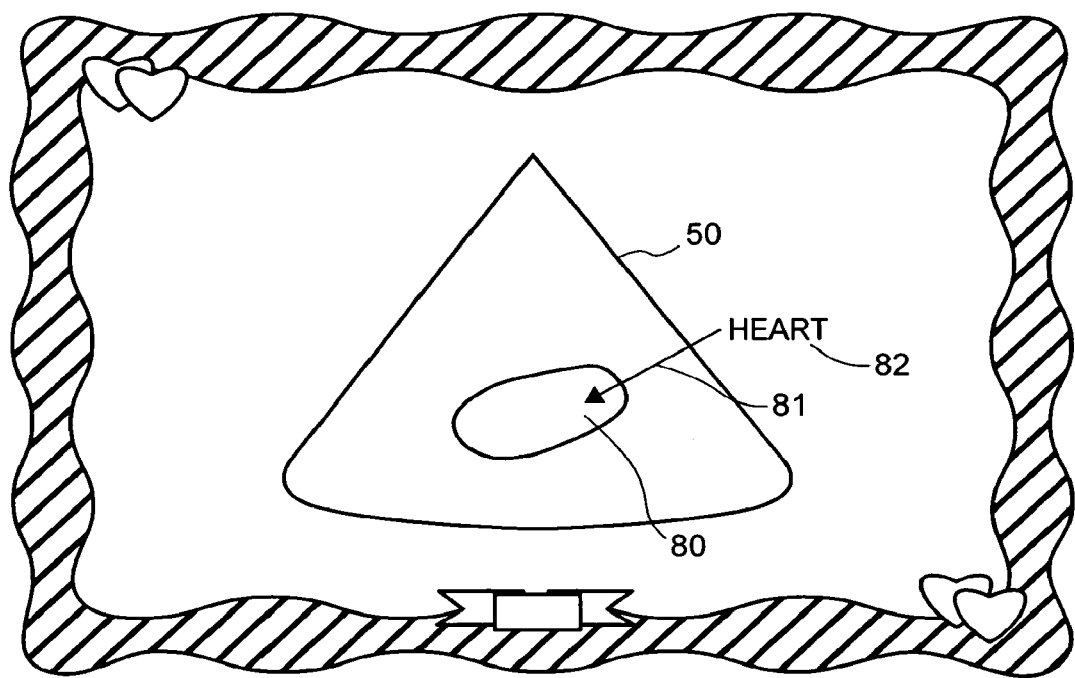
FIG. 8 is an illustration showing an example of annotation superimposed on the ultrasound image.

FIG. 8 is an illustration showing an example of annotation superimposed on the ultrasound image. As shown in FIG. 8, the doctor may annotate a specific part 80 of the diagnosis image 50 with an arrow 81 pointing the specific part 80 and a small comment 82 on the specific part 80. The annotated information is superimposed and displayed on the ultrasound image. This can be made only by the doctor since medical expert knowledge is required to do so. The annotation may be input from the input unit 13 and taken into the main unit 12 through the interface 26. When the annotation is stored as the decorative data in the memory unit 23, the decorative element of the annotation is associated with the image data of the patient since this decorative element is used particularly for the image.

If the annotation position is limited by the arrangement information, the annotation may be made as part of the image data. Since the annotation is usually added as graphical information (or overlay information) and not as a part of an original image data, the image data may include the graphical information of the annotation herein.

Figure 9:
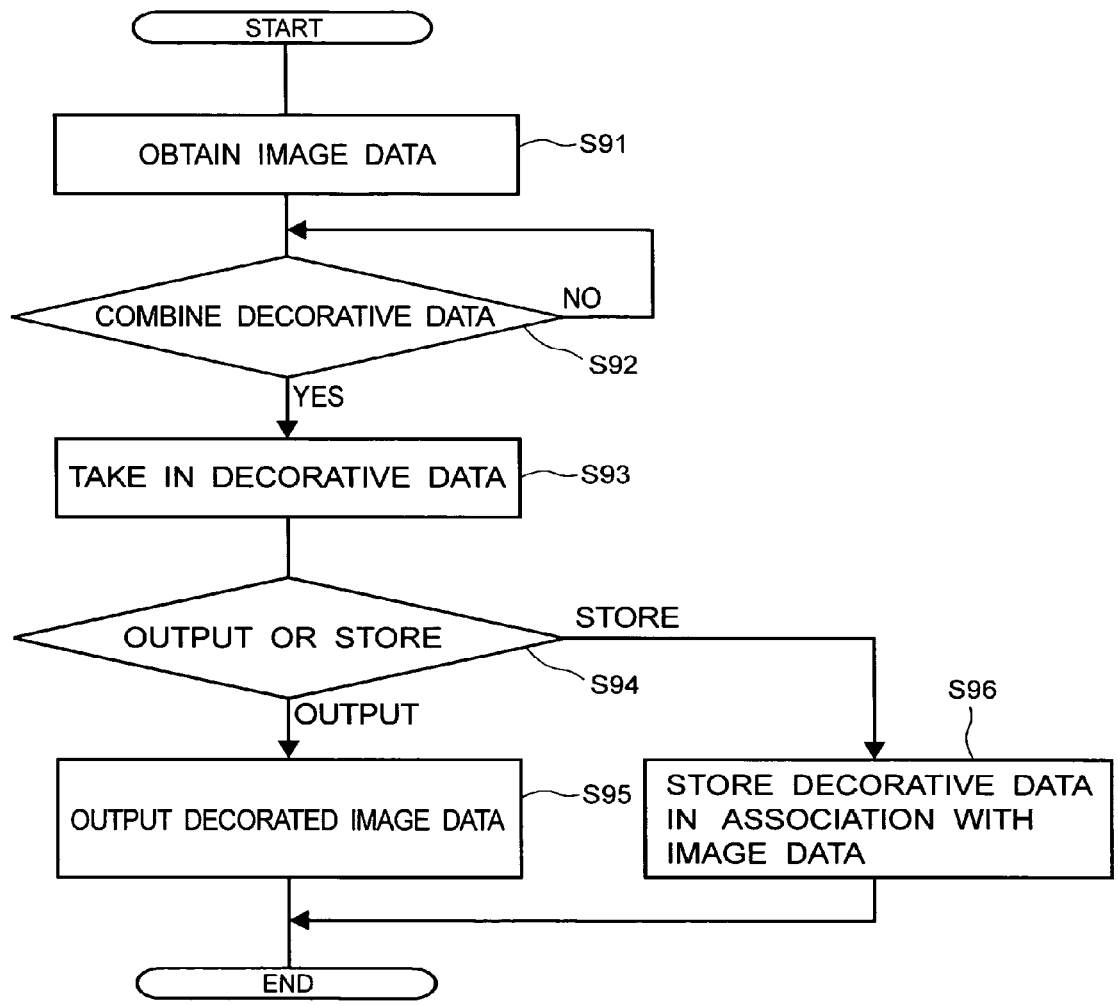
FIG. 9 is a flowchart showing an exemplary flow of another decorated image data preparation in the ultrasound diagnosis apparatus.

FIG. 9 is a flowchart showing an exemplary flow of another decorated image data preparation in the ultrasound diagnosis apparatus. The image data is obtained in a similar manner to step S41 in FIG. 4 (step S91). The doctor can diagnose the patient based on the ultrasound image displayed in the display unit 14 in real time during the ultrasound imaging. Alternatively, however, the doctor operates the input unit 13 to reproduce the stored image data for the ultrasound diagnosis. In response to the doctor's operation, the control unit 25 receives an instruction based on the doctor's operation through the interface 26 and reads the stored image data from the memory unit 23. The image data is provided to the image production processing unit 24 and displayed in the display unit 14 as the ultrasound image (or a reproduced ultrasound image). The doctor then conducts the ultrasound diagnosis based on the reproduced ultrasound image.

Since the ultrasound diagnosis is conducted during a display of the ultrasound images, decorated image data may be prepared (or produced) during the diagnosis. The doctor may select one frame image from among a number of image frames included in the image data by pausing the motion picture at one image frame. After the pause, when the doctor inputs an instruction of combining a decorative image with the selected one frame image from the input unit 13 (step S92), the instruction is provided to the image production processing unit 24 through the interface 13 and the control unit 25. In the following description, the diagnosis image of the image data shows a fetus and the decorative data are photographs of a mother and a father of the fetus and messages. In response to the instruction, the image production processing unit 24 reads the arrangement information from the memory unit 23.

Figure 10:
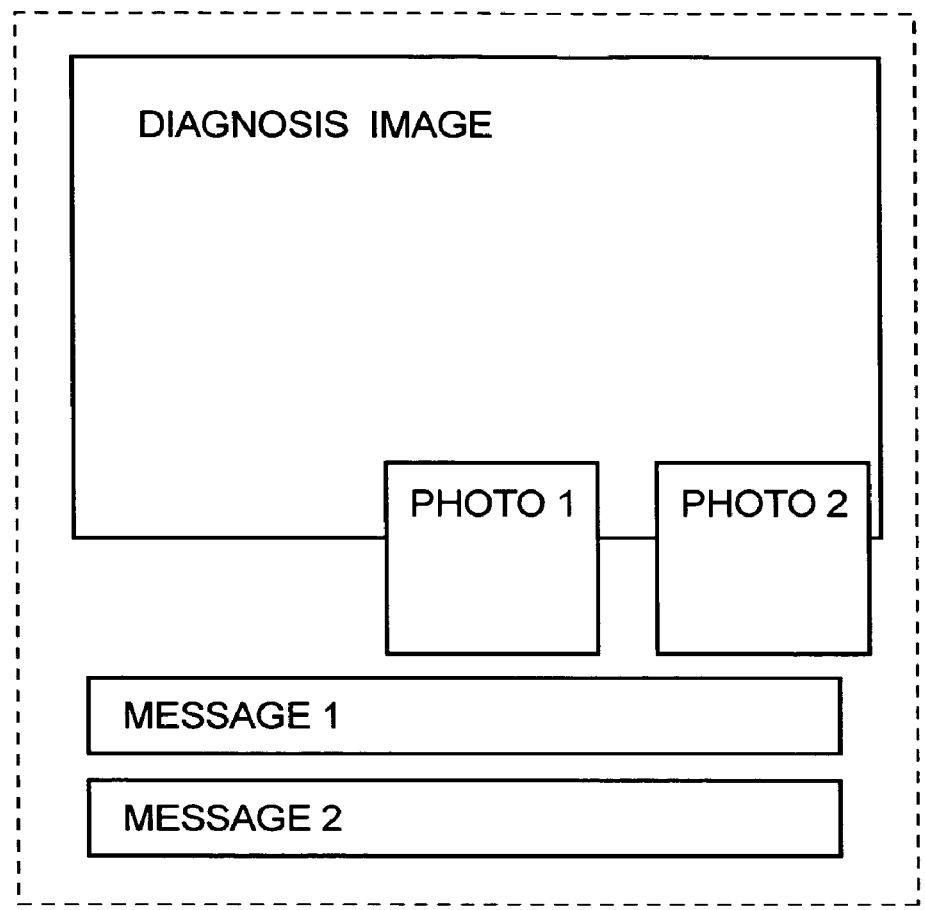
FIG. 10 is an illustration showing an example of arrangement information.

FIG. 10 is an illustration showing an example of the arrangement information. For example, the arrangement information may have a predetermined arrangement format of the image and the decorative elements According to the arrangement information in FIG. 10, the diagnosis image, two photographs, and two messages can be inserted into predetermined positions. The diagnosis image displayed at the time of the combining instruction is inserted into and displayed in the arranged position for the diagnosis image. When a photograph of the mother (i.e., an expecting mother) is taken by a digital camera, the digital photograph may be taken into the main unit 12 through the interface 26. The digital photograph may be provided to the image production processing unit 24 and displayed in the display unit 14. In the display unit 14, the digital photograph may be inserted into and displayed in the arranged position for a photograph 1. Similarly, when a photograph of the father is taken by the digital camera, the digital photograph may be inserted into and displayed in the arranged position for a photograph 2. The photograph of the mother may alternatively be inserted into the arranged position for the photograph 2 if the doctor designates the arranged position for the photograph 2 by, for example, a cursor when the digital photograph is taken in through the interface 26. Similarly, the photograph of the father may be inserted into the arranged position for the photograph 1 by the doctor's designation or automatically due to the designation of the arranged position for the photograph 2 for the photograph of the mother.

The doctor, the mother as the patient, or the father may operate the input unit 13 to designate the arranged position for a message 1. In response to an input of a message from the input unit 13, the input message is provided to the image production processing unit 24 through the interface 26. The input message is inserted into and displayed in the arranged position for the message 1. Similarly, when the doctor, the mother, or the father may desire to input another message, such another message is inserted into and displayed in the arranged position for a message 2 (step S93). Accordingly, a decorated image data is prepared in the image production processing unit 24 in accordance with the arrangement information. That is, the decorated image data may provide a decorated image showing the diagnosis image, the photographs, and the messages arranged as shown in FIG. 10.

When the photographs and the messages have been taken in and the decorated image data has been prepared, the doctor may operate the input unit 13 to instruct an output or storage of the decorated image data (step S94). If the output is instructed, the decorated image data is provided to the printer 15 through the interface 26. The printer 15 prints out a sheet showing the decorated image (step S95). Since the decorated image includes the photographs of the mother and father and the messages, the mother and father given the printed-out sheet could remember this occasion in the future. If the storage is instructed in step S94, the decorated image data is provided to and stored in the memory unit 23 (step S96). In the storage, data of the diagnosis image included in the decorated image may be stored as the image data. The photographs and the messages may be stored as the decorative data separately from the diagnosis image data but in association with the diagnosis image data. The photographs and the messages may also be associated with the arrangement information. When the ultrasound imaging is conducted on the fetus, a record of the fetus growth can be prepared by repeating the imaging and printing/storage periodically. When the stored image data and decorative data are reproduced as the decorated image-data and displayed and/or printed out, the image data and the decorative data are arranged in accordance with the stored arrangement information. Alternatively, the image data and the decorative data may be arranged in accordance with any arrangement information stored in the memory unit 23 at the time of the display/printing.

In the second embodiment, the output is not limited to the printing but may also be conducted in other manners as explained in the first embodiment. In addition, the arrangement information may also include a section named, for example, 'Voice Message' for recording a voice message. In response to designation of the section by the input unit 13, voice messages of the doctor and/or the patient may be recorded through a microphone which is provided in or coupled to the ultrasound diagnosis apparatus. A cardiac sound obtained during the diagnosis may also be recorded. Audio information such as, for example, the recorded voice message and/or the cardiac sound may also be stored in association with the image data or the decorative data. This may be advantageous when the audio information is output to and stored in an IC card or an audio and image reproducible memory medium.

Third Embodiment

Figure 11:
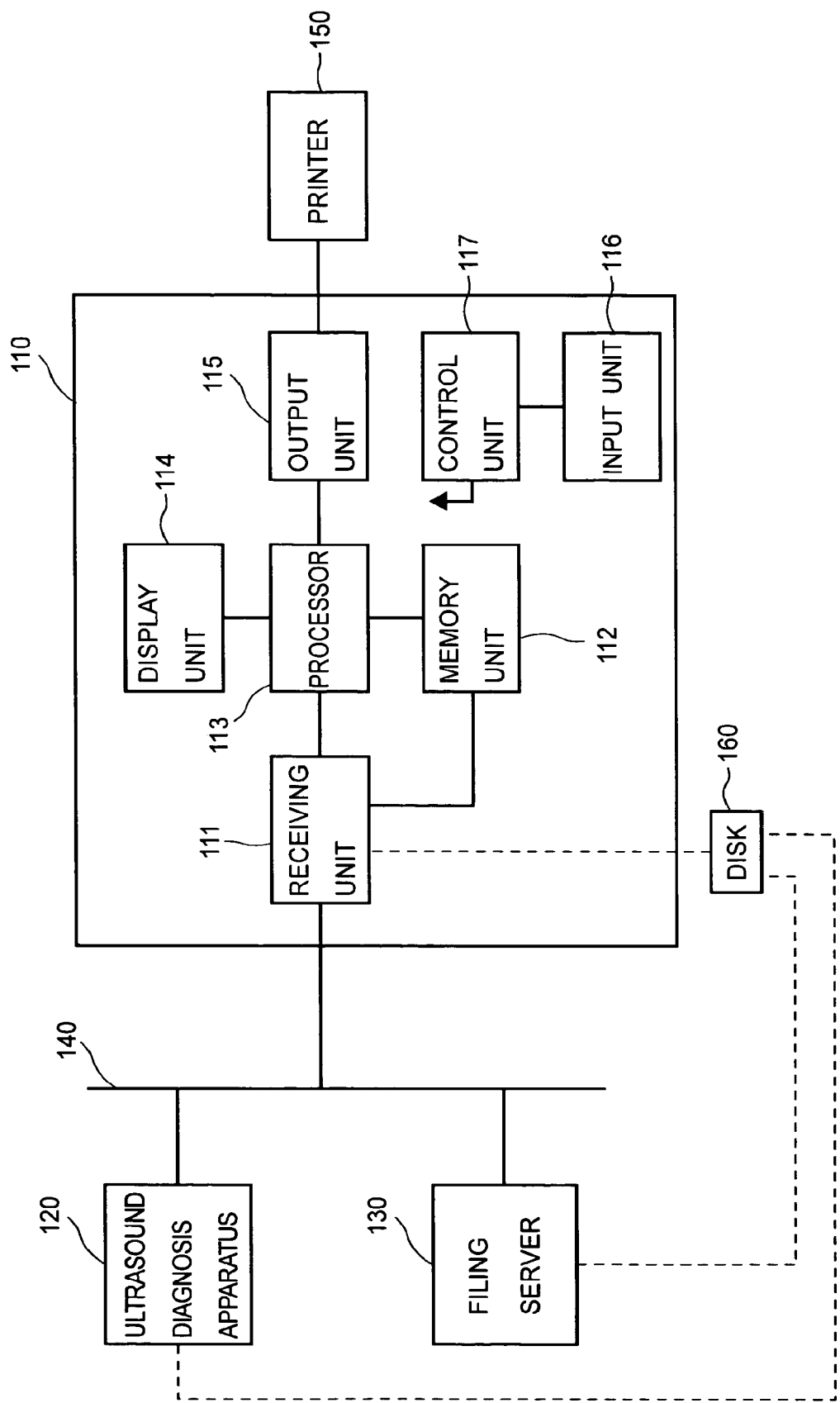
FIG. 11 is a block diagram showing an exemplary configuration of a medical image display apparatus according to the third embodiment.

In the first and second embodiments, the decorated image data have been prepared in the medical imaging apparatus. The decorated image data, however, may also or alternatively be prepared in a medical image display apparatus. FIG. 11 is a block diagram showing an exemplary configuration of the medical image display apparatus according to the third embodiment. The medical image display apparatus maybe a workstation. The medical image display apparatus may be provided in a consultation room. Here, the medical image display apparatus displays the ultrasound images received as the image data generated in the medical imaging apparatus through the network, the memory medium, or the like.

As shown in FIG. 11, a workstation 110 may be connected to an ultrasound diagnosis apparatus 120 and a filing server 130 through a hospital LAN (local area network) 140. The workstation 110 is an example of the medical image display apparatus and may include a receiving unit 111, a memory unit 112, a processor 113, a display unit 114, an output unit 115, an input unit 116, and a control unit 117. The workstation 110 may also be connected to a printer 150. It may also be possible to attach a memory disk 160 to the workstation 110.

The receiving unit 111 receives image data obtained by the ultrasound diagnosis apparatus 120. The receiving unit 111 may receive the image data directly from the ultrasound diagnosis apparatus 120 through the hospital LAN 140 or the image data stored in the filing server 130 from the filing server 130 through the hospital LAN 140. The receiving unit 111 may also receive the image data stored in the memory disk 160 when the receiving unit 111 is operative as a disk driver. The memory disk 160 is an example of a memory medium.

The memory unit 112 stores the received image data and the decorative data. The processor 113 conducts various types of image processing including a combination processing of the image data and the decorative data. The image data may be obtained from the memory unit 112 or, if necessary, from the receiving unit 111. The display unit 114 displays the image data as reproduced ultrasound images as a motion picture or a still frame image. The display unit 114 also displays the combined image data when an operator such as, for example, a doctor operates the input unit 116 to instruct of decorating the image data with the decorative data.

The output unit 115 outputs the combined image data as the decorated image data. For example, the output unit 115 outputs the decorated image data to the printer 150. The printer 150 prints out a sheet showing the decorated image based on the decorated image data. The printer 150 is an example of an output unit. The output of the decorated image data may also be conducted in other manners as explained in the first embodiment.

The input unit 116 is used to input various instructions and information by the operator. The decorative data may be selected and determined in accordance with the instructions from the input unit 116. The decorated image data may be prepared in response to the instructions from the input unit 116.

The control unit 117 controls over the workstation 110. The control unit 117 also controls the processor 113 and the above units based on the instructions and information input from the input unit 116.

The details of preparing the decorated image data described in the first and/or second embodiments may also be applied to the workstation 110. In addition, units and processors which have been described in the first and/or second embodiments and not described in the third embodiment may also be applied to the third embodiment as long as such units and processors are applicable to the third embodiment.

The ultrasound diagnosis apparatus 120 is only an example of a medical imaging apparatus.

When the workstation 110 is used in a consultation room in a hospital, the doctor and the patient can observe the image displayed in the display unit 114 in a more relaxing and calmer condition than during the imaging by the medical imaging apparatus and select one or more appropriate or patient-desired images which the patient takes back home with him/her if the patient desires to do so after the consultation. In this case, the image can be decorated with a decorative image in a manner as described in the first and/or second embodiments.

In any of the first, second, and third embodiments, the decorated image data may easily be prepared by the doctor or the operator. Therefore, it may not take a long time for the doctor to prepare the decorated image data. For the patient, the decorated image(s) may be more interesting, attractive, preferable, and/or appreciated to keep for the commemorative purpose. The patient may be able to select one or more desired images to be decorated if the doctor allows him/her to do so. Such image selection may be possible because this takes place in a medical facility where original image data are kept. Further in a similar sense, the doctor may conduct an extra imaging for obtaining images to be decorated at the discretion of the doctor. The decorated image is printed directly based on the original decorated image data prepared in the medical imaging apparatus or the medical image display apparatus. Therefore, the image quality of the printed decorated image may be better than one obtained by combining decorative data and image data resulting from scanning a once-printed-out image. According to the above reasons, the decorated image preparation may satisfy the patient more than before.

In the above embodiments, the medical imaging apparatus such as, for example, the ultrasound diagnosis apparatus or the medical image display apparatus may have a random access memory (RAM), which can receive and store computer programs and applications as computer readable instructions in a temporary and/or non-volatile state. The above medical imaging apparatus or the medical image display apparatus may further have a hard disk drive as part of the controller for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer readable medium for storing computer readable instructions, which when executed, may implement an embodiment of the present invention.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. A medical imaging apparatus, comprising:
   an imaging unit configured to image a subject;
   an input unit configured to input information of an imaging part of the subject imaged by the imaging unit;
   a first processor configured to prepare image data based on data obtained from the imaging unit;
   a second processor configured to combine the image data and decorative data when the information input by the input unit is of a first part of the subject, but to not combine the image data and the decorative data when the information is of a second part of the subject;
   a display unit configured to display the combined image data; and
   an output unit configured to output the combined image data as decorated image data.

2. The apparatus according to claim 1, wherein the apparatus is portable.

3. The apparatus according to claim 1, wherein the imaging unit is used for an obstetrical service.

4. The apparatus according to claim 1, wherein the apparatus is an ultrasound diagnosis apparatus.

5. The apparatus according to claim 1, wherein the second processor combines the image data and the decorative data by synthesizing the image data and the decorative data.

6. The apparatus according to claim 1, wherein the output unit outputs the decorated image data to a printer coupled to the apparatus.

7. The apparatus according to claim 1, wherein the output unit writes the decorated image data to a memory medium.

8. The apparatus according to claim 1, wherein the output unit transmits the decorated image data through a network.

9. The apparatus according to claim 1, wherein the input unit is configured to enable selection of one of a plurality of image frames as the image data when the imaging unit results in generating the plurality of image frames.

10. The apparatus according to claim 1, wherein the input unit is configured to input arbitrary information, wherein the arbitrary information is superimposed on the image data.

11. The apparatus according to claim 10, wherein the arbitrary information is an annotation information for the image data.

12. The apparatus according to claim 10, wherein the arbitrary information is a comment information.

13. The apparatus according to claim 1, further comprising:
   a memory unit configured to store a plurality of decorative elements; and
   the input unit is configured to select one of the plurality of decorative elements as the decorative data.

14. The apparatus according to claim 1, further comprising:
   a memory unit configured to store one or more decorative elements, each of which being associated with information of one of diagnosis types; and wherein
   the input unit is configured to input information of a designating diagnosis type,
   wherein the second processor determines one of the one or more decorative elements associated with the information of one of the diagnosis types which corresponds to the designating diagnosis type as the decorative data.

15. The apparatus according to claim 4, further comprising:
   a determination unit configured to determine a type of an ultrasound probe when the imaging unit includes the ultrasound probe; and
   a memory unit configured to store one or more decorative elements, each of which being associated with one or more ultrasound probe types,
   wherein the second processor determines one or more of the decorative elements associated with one of the ultrasound probe types which corresponds to the determined type of the ultrasound probe as the decorative data.

16. The apparatus according to claim 15, wherein each of the ultrasound probe types results in a different shape of an image.

17. The apparatus according to claim 1, further comprising a determination unit configured to compare the decorative data to a peripheral part when the image data includes the peripheral part and a subject image part and determine whether the decorative data is applicable to a peripheral part or not, wherein the second processor combines the image data and the decorative data when the decorative data is applicable to the peripheral part.

18. The apparatus according to claim 17, wherein, when the decorative data includes a plurality of decorative elements, the determination unit compares one or more of the plurality of decorative elements to the peripheral part, and the second processor combines the image data and one of the decorative elements as the decorative data when the one of the decorative elements is applicable to the peripheral part.

19. The apparatus according to claim 1, further comprising a determination unit configured to determine whether the image data is applicable to a superimposable part of the decorative data or not, wherein the second processor reduces a size of the image data so that the reduced image data is applicable to the superimposable part when the image data is not applicable to the superimposable part.

20. The apparatus according to claim 19, wherein, when the decorative data includes size information of the superimposable part, the determination unit determines whether the image data is applicable to the superimposable part based on the size information and a size of the image data.

21. The apparatus according to claim 1, further comprising a memory unit configured to store arrangement information indicating where to arrange a plurality of decorative elements of the decorative data with respect to the image data, wherein the second processor combines the image data and the plurality of decorative elements based on the arrangement information.

22. The apparatus according to claim 1, further comprising a memory unit configured to store the image data and the decorative data, the image data being associated with the decorative data.

23. A medical image display apparatus for use in a medical facility, the apparatus comprising:
   a receiving unit configured to receive medical image data;
   an input unit configured to input information of an imaging part of a subject imaged in obtaining the medical image data;
   a memory unit configured to store decorative data;
   a processor configured to combine the medical image data and the decorative data when the information input by the input unit is of a first part of the subject, but to not combine the image data and the decorative data when the information is of a second part of the subject;
   a display unit configured to display the combined image data; and
   an output unit configured to output the combined image data as decorated image data.

24. A method of providing an image data, the method comprising:
   imaging a subject in a medical imaging apparatus;
   inputting information of an imaging part of the subject imaged in the imaging step;
   preparing the image data based on the imaging;
   combining the image data and decorative data only when the information input in the inputting step is of a first part of the subject, but not combining the image data and the decorative data when the information is of a second part of the subject;
   displaying the combined image data when the combining step combines the image date and the decorative data; and
   outputting the combined image data as decorated image data.

25. A computer readable medium on which is stored a program module for providing image data obtained by a medical imaging apparatus, the program module comprising instructions, which when executed perform steps comprising:
   obtaining decorative data;
   inputting information of an imaging part of a subject imaged in the obtained image data;
   combining the image data and the decorative data only when the information input in the inputting step is of a first part of the subject, but not combining the image data and the decorative data when the information is of a second part of the subject;
   displaying the combined image data when the combining step combines the image date and the decorative data; and
   outputting the combined image data as decorated image data.

* * * * *